US006770447B2

(12) United States Patent
Maynard et al.

(10) Patent No.: US 6,770,447 B2
(45) Date of Patent: Aug. 3, 2004

(54) OPTICAL ASSAY DEVICE AND METHOD

(75) Inventors: James E. Maynard, Boulder, CO (US); Mark A. Crosby, Boulder, CO (US); Alan J. Fujii, Newport Beach, CA (US)

(73) Assignee: Thermo Biostar, Inc., Louisville, CO (US)

( * ) Notice: Subject to any disclaimer, the term of this patent is extended or adjusted under 35 U.S.C. 154(b) by 368 days.

(21) Appl. No.: 09/905,146

(22) Filed: Jul. 12, 2001

(65) Prior Publication Data

US 2002/0064888 A1 May 30, 2002

Related U.S. Application Data

(62) Division of application No. 09/272,641, filed on Mar. 18, 1999, now Pat. No. 6,287,783.

(51) Int. Cl.[7] ....................... G01N 33/53; G01N 33/543

(52) U.S. Cl. ............................ 435/7.1; 422/55; 422/56; 422/57; 422/58; 422/61; 422/82.05; 422/82.08; 435/287.1; 435/287.2; 435/287.7; 435/287.8; 435/287.9; 435/808; 435/810; 436/164; 436/165; 436/169; 436/170; 436/172; 436/518; 436/530; 436/531; 436/805

(58) Field of Search ............................... 422/55–58, 61, 422/82.05, 82.08; 435/287.1, 287.2, 287.7, 287.8, 287.9, 810, 808, 7.1; 436/164, 165, 169, 172, 170, 805, 518, 530, 531

(56) References Cited

U.S. PATENT DOCUMENTS 4,246,339 A 1/1981 Cole et al. ..................... 435/7
4,623,461 A 11/1986 Hossom et al. ............... 514/58
4,632,901 A 12/1986 Valkirs et al. ................. 435/5
4,693,834 A 9/1987 Hossom ...................... 210/767
4,727,019 A 2/1988 Valkirs et al. ................. 435/5
4,789,526 A 12/1988 Matkovich .................. 422/101
4,963,325 A 10/1990 Lennon et al. ................ 422/61
4,976,926 A 12/1990 Matkovich .................. 422/101
5,006,309 A 4/1991 Khalil et al. .................. 422/56
5,008,080 A 4/1991 Brown, III et al. ........... 422/56
5,137,691 A 8/1992 Parker ......................... 422/58
5,160,701 A 11/1992 Brown, III et al. ........... 422/56
5,212,065 A 5/1993 Pegg et al. .................... 435/7
5,418,136 A 5/1995 Miller et al. .................. 435/5

FOREIGN PATENT DOCUMENTS

EP 0 186 100 7/1986
EP 0 451 686 A2 10/1991

*Primary Examiner*—Christopher L. Chin
(74) *Attorney, Agent, or Firm*—Foley & Lardner LLP

(57) ABSTRACT

The present invention involves an optical assay device and method of use for the detection of an analyte of interest in a sample that conveniently allows control of the flow characteristics of the sample through the device without significant user intervention. The optical assay device includes a base having an absorbent material, and a member having an optically active test stack that is rotatably coupled to the base for rotation between a lowered position and a raised position. In the lowered position, the optically active test stack contacts the absorbent material for drawing the sample through the surface. In the raised position, the optically active test stack does not contact the absorbent material.

3 Claims, 3 Drawing Sheets

OPTICAL ASSAY DEVICE AND METHOD

This application is a divisional of U.S. application Ser. No. 09/272,641, filed Mar. 18, 1999, now U.S. Pat. No. 6,287,783.

FIELD OF THE INVENTION

The invention relates, in general, to methods and devices useful for analytical testing and, in particular, to methods and devices for flow-through optical assay.

BACKGROUND

An optical assay device is a device used to detect an analyte such as an antigen. These devices may carry an optically active test member to which a sample is applied for determining the presence or amount of an analyte of interest.

It is desirable in an assay device for the optically active test member to be extremely sensitive to the existence of an analyte, and for the assay performance time, i.e., incubation time, to be as short as possible. This is accomplished in flow-through optical assay devices by maximizing the sample volume which is brought in contact with an analyte specific receptive material or the test member and controlling the flow characteristics of the sample through the optical member.

Although the sample will flow through the optical member without external assistance, the flow characteristics of the sample across the optical member and through channels within the optical member or around the optical member can be modified by the use of absorbent materials. Absorbent material allows for wicking which acts to draw fluid from the surface that the adsorbent material is in contact with which can cause fluid to be drawn across the layers of the optical member and through the channels within the optical member or around the optical member. The absorbent material also provides drying of the optical member when contacted with the optical stack. This drying helps to distinguish the signal produced by the optical member.

U.S. Pat. No. 5,418,136 (Miller et al.) describes a blotting device and blotting method which uses an optically reactive surface as the receptor for samples and reagents related to the particular assay being performed. The device contains an optically reactive layer supported on a pedestal of the device in order to allow placement of various solutions, e.g. sample, washing reagents, substrate, directly onto the reactive layer's top surface. The solutions are removed by blotting the reactive surface with an absorbent material by physically pressing the absorbent material onto the reactive surface.

These optical assay devices require that the user apply a discrete volume of sample (approximately 25–30 $\mu$L) on the surface and that the incubation times be controlled by user intervention. Sample incubates on the surface in a static mode as the surface is solid and impermeable. The drying process also requires user interaction to bring the adsorbent material into contact with the solid optical test surface from above the test surface. While the solid surface optical assays are extremely sensitive, an improvement in sensitivity can be gained by using all of the available sample (dependent on sample processing but generally greater than 200 $\mu$L). In many testing sites, the requirement for user intervention in timing and drying the optical test device is inconvenient and not cost effective.

The prior art also includes assay devices that allow for sample flow through the surface of a porous material or across a tortuous path material. Detection is based on the generation of a calorimetric signal through the use of a chromophore or a light scattering particle and signal generation is external to and independent of the surface characteristics of the porous support. In these assays, sample flows through the device with a very limited contact time with the capture element of the device. Thus, sensitivity of the assay is limited by the capture efficiency of the system. Many of these devices suffer from highly variable flow rates as minor changes in the sample composition occur.

The devices of the current invention allow the sample incubation to occur over a period of time to improve capture efficiency but also minimize the user intervention required to complete the assay. The devices also provide an increase in assay performance by allowing all available sample to flow across the optical member and through channels within the optical member. Because the contact time of sample with the test surface is controlled, the devices are less sensitive to variable flow rates than other prior art devices. Also in the devices of this invention, the signal generation is inherent in the composition and construction of the flow through support. Drying of the optical surface from below instead of from above decreases the risk of damaging the optical surface prior to the detection step.

SUMMARY OF THE INVENTION

To this end, an aspect of the present invention involves an optical assay device for the detection of an analyte of interest that conveniently allows the device, not the user, to control the flow rate and mass transport of a sample, i.e., any fluid medium, gas or liquid, through the device. The optical assay device includes a base having an absorbent material, and a member having an optically active test membrane or stack that is rotatably coupled to the base for rotation between a lowered position and a raised position. The optically active test stack includes all of the components necessary to generate the optical signal on the test surface including the capture reagent and to allow for sample flow. In the lowered position, the optically active test stack contacts the absorbent material for drawing the sample across the optical member and through channels within or around the optical member. In the raised position, the optically active test stack does not contact the absorbent material and allows for increased sample contact time with optical test surface.

This simple control feature improves analyte capture efficiency by increase sample contact time with the capture reagent and for rapid fluid flow. The control feature is a simple manually operated rotation of the device that minimizes user interaction while allowing for the execution of a number of assay manipulations.

In a preferred embodiment of the present invention, the optical assay device may include any or all of the following:

- the member is rotatably coupled to the base through a cam mechanism, the cam mechanism including at least one ramp, whereby the member moves up at least one ramp when the member is moved from the lowered position to the raised position, and down at least one ramp when the member is moved from the raised position to the lowered position;
- the optical assay device also includes a retaining mechanism for retaining the member to the base;
- the optical assay device also includes a stop mechanism for restraining the rotation of the member to the lowered position, the raised position, and therebetween;
- the member includes a projection adapted to be manipulated by a user's fingers to assist in rotating the member;

the base includes a pair of finger grips to assist in holding the base;

the optically active test stack includes an optically functional layer made of an amorphous silicon or other material to make the test surface reflective and having a thickness between 1000 and 5000 Å;

a support carries the optically active test stack, the support preferably made of nylon, track-etch polycarbonate, nitrocellulose, or polysulfone;

the optically functional layer is coated with an antireflective layer having a thickness between 400 and 700 Å; and the antireflective layer is coated with an attachment layer made of a diamond-like carbon (alternatives to diamond-like carbon include thin layers of Ni, Ge, or polymers like siloxones or film forming latexes) having a thickness between 50 and 1000 Å.

Another aspect of the present invention involves an optical assay device that includes a base having absorbent material, and a member including an optically active test stack. The base lies generally in a first plane, and the member lies generally in a second plane that is parallel to the first plane. The member is operatively associated with the base for movement between a lowered position and a raised position. In the lowered position, the optically active test stack contacts the absorbent material and the member lies generally in the same plane as the base for drawing a sample through the stack. In the raised position, the optically active test stack does not contact the absorbent material and the member does not lie in the same plane as the base.

If sample is applied with the member in the lowered position, flow will initiate immediately. This is advantageous in an assay system where extremely high sensitivity is not required. The sample will flow until exhausted and then wash can be directly applied to the member in the lowered position. Additional reagents can be applied to the member in the lowered position until the assay is complete. An alternative would be to add a reagent, preferably the amplification reagent, to the member in the raised position. In this case, the amplification reagent will incubate on the optically active surface until the member is moved into the lowered position for removal of the amplification reagent and a final wash prior to read.

In assay systems where sensitivity is a requirement, the sample should be applied with the member in the raised position to allow for efficient capture of the available analyte. After the incubation period, the sample flow is initiated by moving the member to the lowered position. The member will remain in the lowered position until the wash step is complete. Then the member will be moved to the raised position for the addition of other reagents. The member remains in the raised position until the incubation period is complete and then is moved to the lowered position to remove reagent and wash the test surface. If necessary the reagent cycle could be repeated until the assay is complete.

A further aspect of the present invention involves an optical assay device for the detection of an analyte of interest that includes a base having absorbent material, and a generally circular member including a central axis. The generally circular member includes a central aperture and an optically active test stack that covers the aperture. The generally circular member is rotatably coupled to the base through a cam mechanism for rotation about the axis between a lowered position and a raised position. In the lowered position, the optically active test stack contacts the absorbent material for drawing a sample through the stack. In the raised position, the optically active test stack does not contact the absorbent material. The optical assay device further includes a stop mechanism for restraining rotation of the generally circular member between the lowered position and the raised position, and a retaining mechanism for retaining the generally circular member to the base.

In a preferred embodiment of the aspect immediately described above, the cam mechanism includes a plurality of ramping members extending from the base, and a plurality of respective ramping members extending from the generally circular upper member that are adapted to slidably cooperate with the ramping members upon rotation of the generally circular member for raising and lowering the generally circular member; and the base includes a well that carries the absorbent material.

Another aspect of the present invention includes an optical assay device including a base having absorbent material, and a member including an optically active test stack. The device further includes means for raising and lowering the member between a lowered position and a raised position. In the lowered position, the optically active test stack contacts the absorbent material for drawing a sample through the surface. In the raised position, the optically active test stack does not contact the absorbent material.

In a preferred embodiment of the aspect immediately described above, the optical assay device includes means for retaining the member to the base.

A still further aspect of the present invention involves a method for detecting an analyte of interest in a test sample. The method includes providing an optical assay device, the optical assay device comprising a base including absorbent material, and a member including an optically active test stack, the member rotatably coupled to the base for rotation between a lowered position where the optically active test stack contacts the absorbent material and a raised position where the optically active test stack does not contact the absorbent material; providing the optical assay device in the lowered position where the optically active test stack contacts the absorbent material for drawing a sample through the stack; applying the test sample to the optically active test stack; applying a conjugate to the optically active test stack; applying a wash to the optically active test stack; rotating the member to the raised position where the optically active test stack does not contact the absorbent material; applying an amplifying reagent in solution to the optically active test stack; rotating the member to the lowered position so that the solution containing the amplifying reagent is drawn through the optically active test stack, thereby depositing the amplifying reagent; and observing the optically active test stack for a visual indication of the presence of the analyte of interest.

Other features and advantages of the inventions are set forth in the following detailed description and drawings, which are intended to illustrate, but not limit, the invention.

DESCRIPTION OF THE PREFERRED EMBODIMENTS

Figure 1:
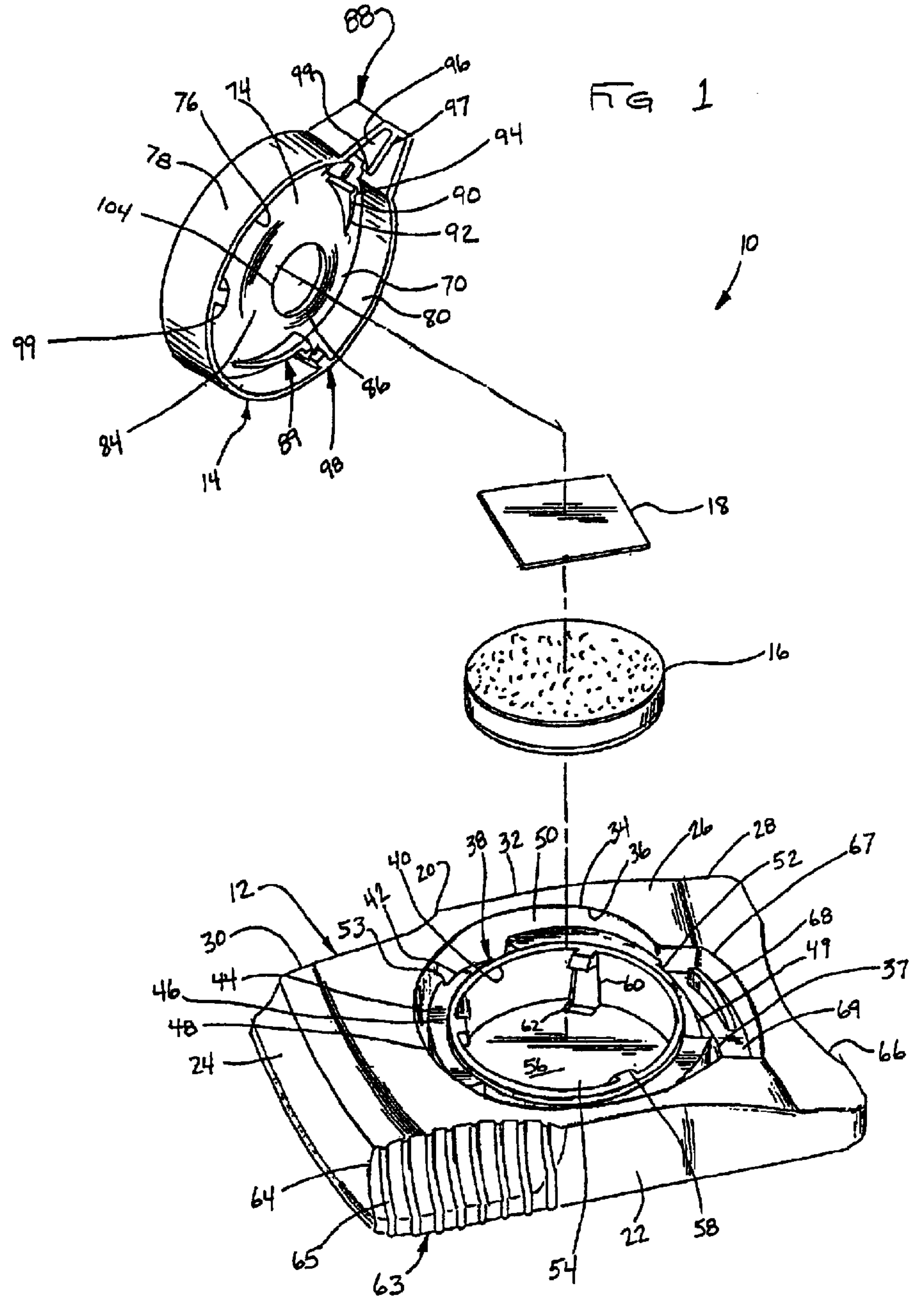
FIG. 1 is an exploded perspective view of an optical assay device constructed in accordance with a preferred embodiment of the present invention.

With reference generally to FIGS. 1–8, and initially to FIG. 1, an optical assay device 10 constructed in accordance with a preferred embodiment of the invention, will now be described. The optical assay device 10 comprises a base 12 and a generally round member 14. The base 12 carries an absorbent material 16, and the member 14 carries a test membrane or optical stack 18. The optical stack 18 may be a stack of one or more materials. The materials may include a combination of materials such that one is quick wetting but poorly absorbent and another is highly absorbent but slow in wetting, or any combination thereof that is consistent with flow and fluid retention requirements.

Figure 3:
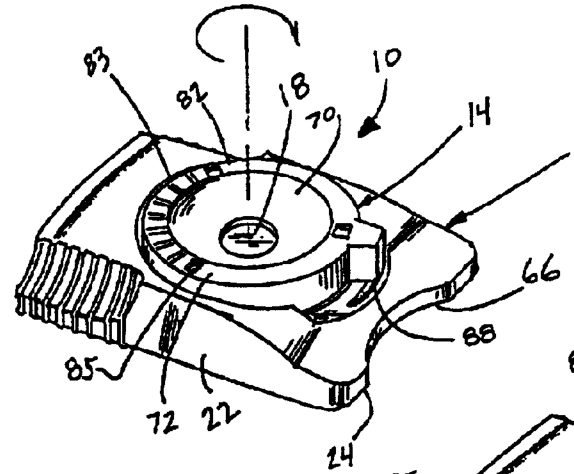
FIG. 3 is a perspective view of the optical assay device illustrated in FIG. 1, and shows the generally round member in a raised position.
Figure 2:
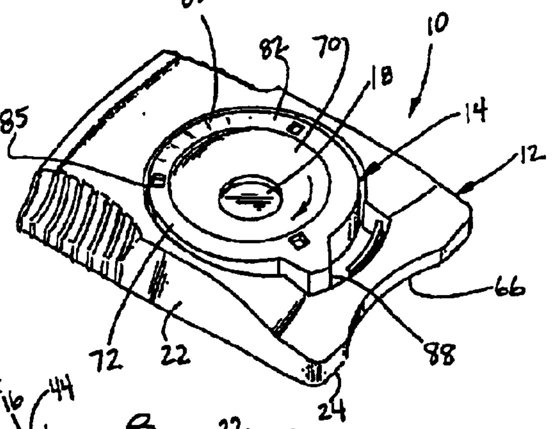
FIG. 2 is a perspective view of the optical assay device illustrated in FIG. 1, and shows the generally round member in a lowered position.
Figure 4:
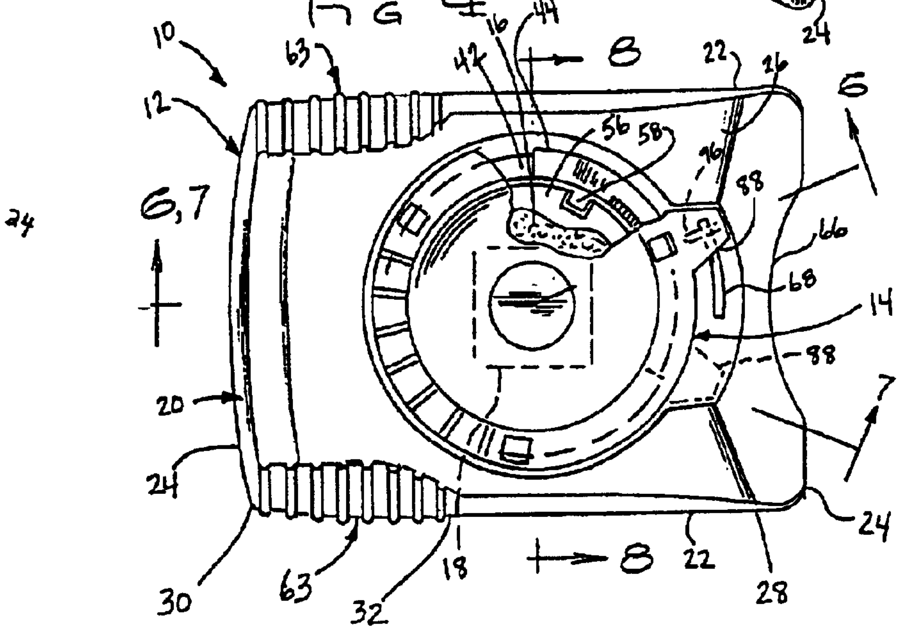
FIG. 4 is a top plan view of the optical assay device illustrated in FIG. 1, and shows the generally round member in the raised position in phantom and an absorbent material and a bottom surface of the device broken-away.
Figure 5:
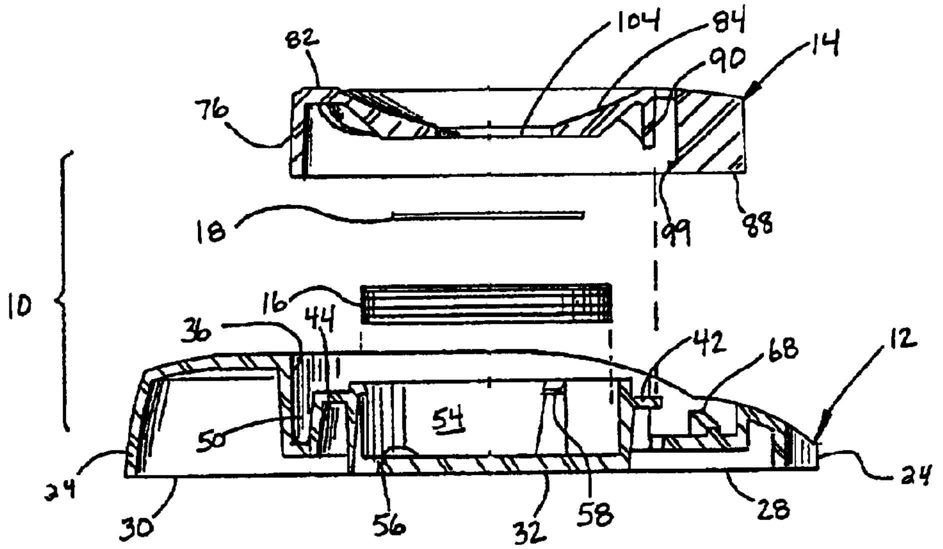
FIG. 5 is an exploded cross-sectional view of the optical assay device illustrated in FIG. 1.
Figure 6:
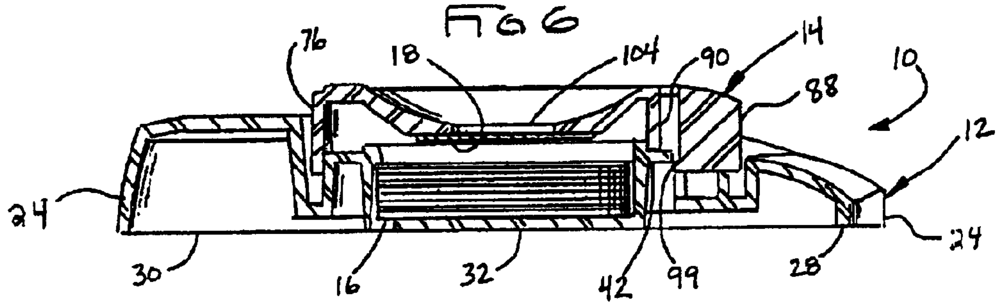
FIG. 6 is a cross-sectional view of the optical assay device of FIG. 4 with the generally round member in the shown lowered position taken along lines 6—6 of FIG. 4.
Figure 7:
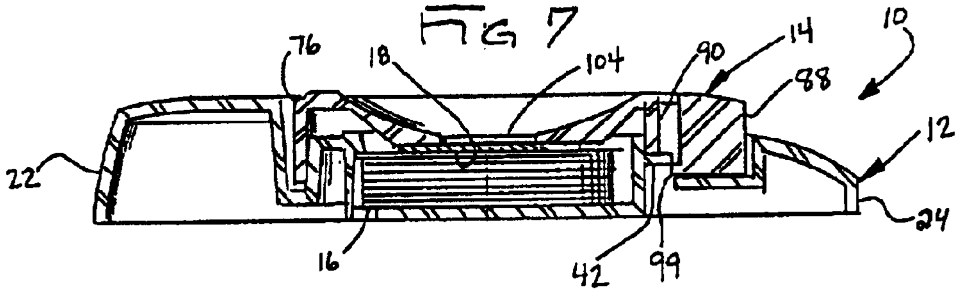
FIG. 7 is a cross-section view of the optical assay device of FIG. 4 with the generally round member in raised position, which is shown in phantom in FIG. 4, taken along lines 7—7 of FIG. 4.
Figure 8:
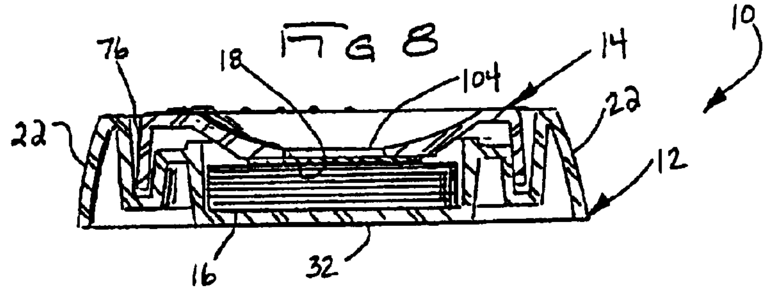
FIG. 8 is a cross-section view of the optical assay device of FIG. 4 with the generally round member in raised position, which is shown in phantom in FIG. 4, taken along lines 8—8 of FIG. 4.

The member 14 is rotatably coupled to the base 12 for rotation between a lowered position (FIGS. 2, 7, 8) and a raised position (FIGS. 3, 6). In the lowered position, the optical stack 18 contacts the absorbent material 16 to alter the natural flow characteristics of a sample across and through the optical stack 18. In the raised position, the optical stack 18 does not contact the absorbent material 16.

By "sample" is meant any fluid medium, gas or liquid. Samples may be used which are high in dissolved solids without further processing and samples containing high solids (non-dissolved) may be introduced through a filter or used in conjunction with additional manual steps. Samples may be a gas, a liquid, a suspension, extracted or dissolved sample, or a supercritical fluid. Some flow properties must exist in the sample.

With reference back to FIG. 1, the base 12 includes a generally rectangular frame 20 having opposite sides 22, opposite ends 24, and top wall 26. The frame 20 includes a front portion 28, a rear portion 30, and a central portion 32. The base 12 lies generally in a first plane. It an alternative embodiment of the invention, the base 12 may include a shape such as, but not limited to, square, circular, or cylindrical.

The central portion 32 includes an outer well 34 bounded by a first circular inner wall 36 and floor 37 of the frame 20.

A first circular ramp or cam assembly 38 is concentric with a first circular inner wall 36. The ramp assembly 38 includes three ramps 42 separated by three corresponding supports 44. Each support 44 includes a flat upper surface 46 and an outer wall 48. Each ramp 42 includes an inclined portion 49 and a flat portion 52.

The ramps 42 are more narrow than the supports 44. Consequently, at opposite ends of each ramp 42, a stop 53 is formed.

A circular groove 50 exists between the first circular inner wall 36 and the ramp assembly 38. An inner well 54 that is concentric with the other well 34 is bounded by the second inner wall 40 and a bottom surface 56. Retaining tabs 58 extend inwardly from the second inner wall 40. The inner wall 40 includes recessed portions 60 below each of the retaining tabs 58. Respective holes 62 are located in the bottom surface 56 at a bottom end of the recessed portions 60.

At the rear portion 30 of the base 12, a pair of finger grips 63 are located at the sides 22. The finger grips 63 comprise sloped, incurved faces 64 with multiple ribs 65 extending therefrom to assist the user in gripping the base 12 with his or her fingers to support it.

A front portion 28 of the base 12 includes an incurved cut-out 66. The frame 20 also includes a recessed area 67 behind the incurved cut-out 66. The recessed area 67 includes a ramp 68 extending from a bottom surface 69. The recessed area 67 communicates with the outer well 34.

The absorbent material 16 is carried by the base 12 in the inner well 54, and retained therein by the retaining tabs 58. The absorbent material 16 comprises a cylindrical stack of absorbent papers sewn together. The absorbent material 16 consists of, from top to bottom, a layer of Tetko Nylon 3-20/14 (Depew, N.Y.), three layers Whatman Chrom 20 paper (Fairfield, N.J.), and two layers of Whatman F4207-07 absorbent (Fairfield, N.J.). The layers were die cut into 1 inch diameter disks for use in the assay device. The stack may be sewn together or may be attached by heat staking or adhesives. The stack may also be physically retained together within the device. The attachment mechanism for attaching the layers together is selected to maintain the flow characteristics of the stack without introducing a biocompatability or stability issue. The materials within the stack must not be wrinkled or torn in the attachment process. Physical contact between the rapidly wetting materials is one of the most important properties for the stack so attachment of these materials is required. However, the highly absorbent waste reservoirs may remain unattached. One or more of these materials may be eliminated or replaced based on the desired flow characteristics for a particular assay and the amount of reagent and sample waste generated in the assay. Materials can also be added to the upper surface of the stack that provide for uni-directional flow of fluid away from contact with the optical stack but above the absorbent stack.

The flow characteristics of the optical stack 18 can be controlled with the absorbent material 16. The flow characteristics of interest are the flow rate across and through the optical stack 18, the retention of fluid at the optical surface, and uniform flow of sample solution over the surface. The flow characteristics of the optical stack are important for ensuring proper reaction time and dryness.

The flow characteristics of the optical stack 18 can be controlled by increasing or decreasing the absorbance of the absorbent material 16, and by controlling contact of the optical stack 18 with the absorbent material 16. When the member 14 is in the lowered position (FIGS. 2, 7, 8), the optical stack 18 contacts the absorbent material 16. Contact with the optical stack 18 causes the absorbent material to draw, i.e., wick, and retain the sample away from the surface of the optical stack 18 that the absorbent material is in contact with. The physical contact of a highly absorbent material with the charnels of the optical stack containing fluid is sufficient to cause flow away from the optical stack. When the round member 14 is in the raised position (FIGS. 3, 6), the optical stack 18 does not contact the absorbent material 16. The applied sample flows across and through the layers of the optical stack 18 when the optical stack 18 does not contact the absorbent material, but at a lower rate compared to when the optical stack 18 contacts the absorbent material 16.

The generally round member 14 includes a generally circular well 70 having a circular ledge 72, a sloped inner portion 84 with a central aperture 86 and an undersurface 74, and a generally circular side wall 76 with an outer surface 78 and an inner surface 80. The circular ledge 72 has multiple striations 83 and three holes 85 located thereon. In an alternative embodiment, the member 14 may have a shape other than round such as, but not limited to rectangular, square, or cylindrical. The generally round member 14 includes a projection 88 that is manipulated by the user's fingers for rotating the member 14 between the lowered position and the raised position. The member 14 lies generally in a second plane that is parallel with the first plane that the base 12 generally lies within.

A second circular ramp or cam assembly 89 including three ramps 90 extends from the lower surface 74 of the well 70. Each ramp 90 includes an inclined portion 92 and a flat portion 94.

The projection 88 includes a rib 96 extending from the lower surface 74 of the well 70 and the inner surface 80 of the side wall 76. The rib 96 has a lower edge 97.

The optical assay device 10 includes a retaining mechanism 98 for retaining the member 14 to the base 12 in a manner described below. The retaining mechanism 98 comprises three retaining members 99. Two of the retaining members 99 project inwardly from the inner surface 80 of the side wall 76 and one of the retaining members 99 projects inwardly from the rib 96 of the projection 88.

A flat peripheral ledge 104 extends along the periphery of the central aperture 86.

The optical stack 18 is fixed to the flat peripheral ledge 104 on the lower surface 74 of the well 70 by fusion, e.g., a heat staking process, glue, two-sided tape, or the like, so that a leak-proof seal is created between the peripheral ledge 104 and the top surface of the optical stack 18.

The optical stack 18, which is constructed in accordance with a preferred embodiment of the invention, will now be described. The optical stack 18 includes one or more components necessary to generate the optical signal on the test surface including the capture reagent and allow for sample flow. It will be readily understood by those skilled in the art that the optical stack 18 may take other forms, such as, but not by way of limitation, that described in U.S. application Ser. Nos. 08/950,963 and 08/742,255, which are incorporated by reference herein as if set forth in detail. The optical stack 18 preferably comprises a support or membrane, an optically functional layer, an attachment layer, and may or may not contain an analyte specific receptive layer.

The support or membrane may comprise any surface on which an assay for an analyte can be performed, and which can be made to support fluid flow including, but not limited to, ceramics, metals, slides, diffraction gratings for surface plasmon resonance, membranes, filter paper, silicon, glass, piezoelectric structures for resonance or oscillation studies, and any compatible surface/detection system combinations. Coatings can be applied uniformly over the surface of the support or in unmasked areas of the support. Supports may be in a range of shapes and configurations.

The following materials are suitable for the production of the support: track-etch polyester, nitrocellulose, cellulose acetate, PETE, polyesters, polycarbonates, glass particles, silica particles, $TiO_2$ particles, metal and non-metal particles, woven and non-woven materials, nylon, filter paper, membranes, polysulfones, porous glass, polypropylenes, polyurethanes, polycarbonates, or any polymer, plastic, and metals or non-metals or composites of these materials. Of these materials, nylon, track-etch polyester nitrocellulose, and polysulfone are preferred for the exemplary application of the device 10 described below.

The optically functional layer can be provided on the support by a thin film coating process. The optically functional layer is a layer which can produce a signal upon the binding of analyte to a receptive layer. The optically functional layer is selected based on the application of the device and the method of analysis used to interpret the assay results. The layer may have one or more coatings, including a base layer with or without one or more antireflective (AR) layers. The optically functional layer is designed to modify the optical properties of the support material so that the desired degree of reflectivity, transmittance, and/or absorbance is suited to the final assay configuration and method of detection. The optically functional layer may attenuate one or more, or a range of wavelengths of light so that the result is observable visually, or by instrumented analysis in the final device upon analyte binding. The attenuation of the light may involve extinction or enhancement of specific wavelengths of light as in an antireflective optical stack for a visually observable color change, or the intensity of a specific wavelength of light may be modified upon reflection or transmittance from the optical stack device. The optically functional layer may also modify the optical parameters of the optical stack to allow a change in the state or degree of polarization in the incident light. The optically functional layer on the support creates on the newly formed composite support an inherent optical signal generation capability.

The film materials that may be used for the base optical material include, but are not limited to, amorphous silicon, polycrystalline silicon, lead telluride, titanium, germanium, cobalt, gallium, tellurium, iron oxide, or chromium, or the like. For the exemplary application of the device 10 described below, an amorphous silicon film having a thickness between 1000 and 5000 Å is preferably used as the base optical material.

The optically functional layer may consist of one or more antireflective layer materials to be applied over the base optical material and include, but are not limited to, aluminum oxide, antimony oxide, bismuth oxide, indium oxide, indium tin oxide, tin oxide, silicon monoxide, titanium dioxide, zirconium oxide, silicon nitride, silicon oxynitride, germanium oxides, cobalt oxides, carbon, tantalum oxide, silicon carbide, manganese oxide, zinc sulfide, nickel oxide, zinc oxide, lead sulfide, cadmium sulfide, chromium oxide, as well as most other metal oxides, carbides, nitrides or oxy-nitrides, diamond, or diamond-like carbon. All antireflective materials may be applied by processes known to those skilled in the art. For the exemplary application of the device described below, the antireflective layer has a thickness between 400 and 700 Å.

The optically functional layer may be coated with an attachment layer. The attachment layer is included to provide a stable environment for the retention of an analyte specific receptive material or a means by which the analyte itself is retained. Analyte binding to the specific receptive material on the attachment layer is achieved by either physical or chemical adsorption due to a specific interaction between an analyte and the analyte specific surface. Alternatively, when the analyte binds non-specifically to the attachment layer, analyte is detected through the subsequent specific binding of an analyte specific binding reagent usually contained in an amplifying reagent.

A range of materials well suited as attachment layers include, but are not limited to, silanes, siloxanes, polymers, diamond-like carbon, platinum, nickel, gold and nichrome (89% nickel, 20% chromium). Preferably a diamond-like carbon attachment layer having a thickness between 50 and 1000 Å is used for the exemplary application described below.

Diamond-like carbon is a layer composed of a uniform film or packed particles which consists of diamond (synthetic or natural), monocrystalline diamond, resin type diamond, polycrystalline diamond, diamond-like carbon, amorphous carbon with diamond like properties (hardness and surface energy), amorphous hydrogenated DLC or carbon films, non-crystalline to crystalline carbon films with diamond like properties or diamond-like material with a chemical composition ranging from graphite-like to diamond.

The analyte specific receptive layer, i.e., analyte specific binding reagent, may be a chelator, an antibody, an antigen, a receptor, a ligand, a protein, a nucleic acid, DNA, RNA, enzymes, any biological molecule capable of binding a specific analyte, or analogs or derivatives thereof, and/or a polymer layer.

Coating of the binding reagents can be performed by either dipping the substrate in a tank of the reagents or by spraying the reagents on and rinsing the substrate. Spot coating, ink jetting, air brushing, or other techniques may also be used. The reagents once coated, may or may not need to be overcoated with a stabilizing layer for storage purposes.

It is possible to use a non-specific capture mechanism for detection of analyte. In this assay format, the analyte may adhere to the surface through a number of chemical interactions. Once the analyte binds to the optical stack, a specific reagent is used to detect analyte presence, e.g., an antibody specific for the analyte to which may be attached an additional mass enhancing material.

The optical assay device 10 is manufactured by injection molding the base 12 and generally round member 14 out of the plastic material, fixing the optical stack 18 to the flat peripheral edge 104, providing the absorbent material 16 in the well 54 of the base 12 so that the retaining tabs 58 retain the absorbent material 16 in the well 54, and attaching the generally round member 14 and the base 12. The generally round member 14 is attached to the base 12 by inserting the side wall 76 of the generally round member 14 into the groove 50 of the base 12, and clipping the retaining members 99 over the outside edges of the ramps 42 so that the retaining members 99 are clamped over the ramps 42.

In use, the ramps 42 of the first ramp assembly 38 are slidably engageable with the ramps 90 of the second ramp assembly 89, and the lower edge 97 of the rib 96 is slidably engageable with the ramp 68 of the recessed area 67 to form a ramp mechanism or cam mechanism. The retaining members 99 of the retaining mechanism 98 retain the ramping assemblies 38, 89 in alignment and retain the generally round member 14 to the base 12. In the lowered position (FIGS. 2, 7, 8), the inclined portions 49 of the ramps 42 mesh with the inclined portions 92 of the ramps 90 so that the optical stack 18 contacts the absorbent material 16. In this position, the first plane, i.e., the plane of the base 12, and the second plane, i.e., the plane of the member 14, are generally coplanar, giving the device 10 a compact profile. Contact with the optical stack 18 causes the absorbent material to draw, i.e., wick, and retain the sample away from the surface of the optical stack 18 that the absorbent material is in contact with, affecting the flow characteristics of the optical stack 18, e.g., increasing the flow rate across and through the optical stack 18.

As the generally round member 14 is rotated, the inclined portions 92 of the ramps 90 and the lower edge 97 of the rib 96 climb the ramps 42 and 68, respectively, causing the generally round member 14 to rise vertically. In the raised position (FIGS. 3, 6), the flat portions 94 of the ramps 90 sit on top of the flat portions 52 of ramps 42 so that the inclined portions 92 of the ramps 90 are generally disposed over the supports 44 of the base 12. In the raised position, the optical stack 18 does not contact the absorbent material 16. In this position, the first and the second plane are parallel, but no coplanar. The applied sample flows across and through the layers of the optical stack 18 when the optical stack 18 does not contact the absorbent material, unaffected by the absorbent material 16, but at a much lower rate compared to when the optical stack 18 contacts the absorbent material 16. Surface tension of the fluid in contact with the optical stack may also delay flow through the optical layer.

Although the generally round member 14 is described as movable between a lowered position and a raised position, it will be readily understood by the reader that the terms "lowered" and "raised" are relative terms. Accordingly, in an alternative embodiment of the invention, the member 14 would still be considered "raised" if the base 12 was lowered relative to the member 14. Similarly, the member 14 would still be considered "lowered" if the base 12 was raised relative to the member 14.

Vertical movement and rotation is limited to the lowered and raised positions by the retaining members 99 and the stops 53. In the lowered and raised positions, the retaining members 99 abut the stops 53 to prevent the generally round member 14 from rotating any further than the lowered and raised positions. Thus, the retaining members 99 and stops 53 form a stop mechanism for limiting the movement of the generally round member 14.

Although the cam or ramp mechanism described above for raising and lowering the optical stack 18 against the absorbent material 16 through rotation of the member 14 generally includes three sets of corresponding ramp members, it will be readily understood by those skilled in the art that other cam or ramp mechanism configurations could exist that provide vertical movement of the member 14 through rotation of the member 14, for example, but not by way of limitation, the cam or ramp mechanism may comprise a single circular ramp extending from the base 12 adapted to slidably engage a single circular ramp extending from the member 14.

Controlling contact between the optical stack 18 and the absorbent material 16 through rotation of the member 14 via the projection 88 provides a convenient and easy way for the user to control the flow characteristics and contact time of an applied sample through the optical stack 18, making the device essentially independent of variability in sample flow rates.

Prior art optical assay devices require that the user apply a discrete volume of sample (approximately 25–30 $\mu$L) on the surface and that the incubation times be controlled by user intervention. Sample incubates on the surface in a static mode because the surface is solid and impermeable. The drying process also requires user intervention to bring the adsorbent material into contact with the solid optical test surface. While the solid surface optical assays are extremely sensitive, an improvement in sensitivity can be gained by using the entire sample (dependent on sample processing but generally greater than 200 μL) for testing. In many testing sites, the requirement for user intervention in timing and drying the optical test device is inconvenient and not cost effective.

As discussed above, the prior art also includes assay devices that allow for sample flow through the surface of a porous material or across a tortuous path material. Detection is based on the generation of a colorimetric signal through the use of a chromophore or a light scattering particle and signal generation is external to and independent of the surface characteristics of the porous support. In these assays, sample flows through the device with a very limited contact time with the capture element of the device. Thus, sensitivity of the assay is limited by the capture efficiency of the system. Many of these devices suffer from highly variable flow rates as minor changes in the sample composition occur.

The device of the present invention allows the sample incubation to occur over a period of time to improve capture efficiency and also minimizes the user intervention required to complete the assay. The device provides an increase in assay performance by allowing all available sample to flow across the optical member and through channels within the optical member. Because the contact time of sample with the test surface is controlled, the device is less sensitive to variable flow rates than other prior art devices. Also, in the device of the present invention, the signal generation is inherent in the composition and construction of the flow through support.

If sample is applied with the member 14 in the lowered position, flow will initiate immediately. This is advantageous in an assay application where extremely high sensitivity is not required. The sample will flow until exhausted and then wash can be directly applied to the member 14 in the lowered position. Additional reagents can be applied to the member 14 in the lowered position until the assay is complete. An alternative would be to add a reagent, preferably the amplification reagent, to the member 14 in the raised position. In this case, the amplification reagent will incubate on the optically active surface until the member 14 is moved into the lowered position for removal of the amplification reagent and a final wash prior to read.

In assay applications where sensitivity is a requirement, the sample should be applied with the member 14 in the raised position to allow for efficient capture of the available analyte. After the incubation period, the sample flow is initiated by moving the member 14 to the lowered position. The member 14 will remain in the lowered position until the wash step is complete. Then, the member 14 will be moved to the raised position for the addition of other reagents. The member 14 remains in the raised position until the incubation period is complete and then is moved to the lowered position to remove reagent and wash the test surface. If necessary the reagent cycle may be repeated until the assay is complete.

An exemplary application of the optical assay device 10, e.g., method for detecting an analyte of interest in a test sample using the device 10, will now be described. The method for detecting an analyte of interest will be described in conjunction with infectious disease testing, namely, testing for the chlamydia antigen. However, it will be readily understood by those skilled in the art that the optical assay device 10 may be used in a wide range of applications where analyte capture is required besides infectious disease testing, such as, but not limited to, cancer diagnosis, drug monitoring, environmental testing, therapeutic drug monitoring, DNA testing, and cardiac testing. The device 10 and method of use can also be used in fields as diverse as medical diagnostics and environmental monitoring or food screening and testing applications.

Moreover, the optical assay device 10 may be used in conjunction with analytes besides antigens, such as, but not by way of limitation, antibodies, receptors, ligands, chelates, proteins, enzymes, nucleic acids, DNA, RNA, pesticides, herbicides, inorganic or organic compounds or any material for which a specific binding reagent may be found.

The first step in the procedure for detecting the chlamydia antigen is to extract a potential chlamydia antigen test sample from a swab or urine sample. With the member 14 of the assay device in the raised position, apply 200 μL of extracted sample to the device well 70. The sample is extracted in the manner described in the commercially available CHLAMYDIA OIA test kit, sold by BioStar, Inc. of Boulder, Colo. Immediately add 200 μL of an anti-Chlamydia antibody conjugated to horseradish peroxidase (by the method of Nakane) to the sample in the device well 70.

Once the conjugate is added to the sample, the member 14 is moved to the lowered position. The sample and conjugate mixture is allowed to completely flow through the optical stack 18. This requires between 3–4 minutes, but the user is not required to time the process.

After the sample and conjugate have completely flowed through the surface, 400 μL of a wash solution is applied to the well 70 and allowed to flow through the optical stack 18. This requires approximately 1 minute, but timing is again not required. The wash solution is preferably a Tris buffered saline solution, but could be a buffer such as water, or contain a small amount of detergent.

The member 14 is moved to the raised position and 300 μL of a commercially available precipitating TMB substrate solution is applied to the well 70. The substrate is allowed to react with the optical stack for 5 minutes. The member 14 is then moved to the lowered position, and the substrate allowed to flow through the optical stack 18. A 400 μL volume of wash is applied and allowed to flow through the optical stack 18. This requires approximately 1 minute. The surface is allowed to dry and the optical stack is observed for a visual indication of the presence of the chlamydia antigen.

Although this invention has been described in terms of certain preferred embodiments, other embodiments apparent to those of ordinary skill in the art are also within the scope of this invention. Accordingly, the scope of the invention is intended to be defined only by the claims that follow.

What is claimed is:

1. A method for detecting the presence or amount of an analyte of interest in a test sample, comprising:

providing an optical assay device, said optical assay device comprising a base comprising absorbent material, and a member comprising an optically active test stack, said member rotatably coupled to said base for rotation between a lowered position where said optically active test stack contacts said absorbent material and a raised position where said optically active test stack does not contact said absorbent material;

applying said test sample to said optically active test stack, wherein said member is in said lowered position;

applying a conjugate that binds to the analyte on to said optically active test stack;

applying a wash to said optically active test stack;

rotating said member to said raised position;

applying an amplifying reagent solution that amplifies a visual indication of the presence or amount of said analyte on said optically active test stack;

rotating said member to said lowered position; and observing said optically active test stack for the visual indication of the presence or amount of the analyte of interest.

2. A method for detecting the presence or amount of an analyte of interest in a test sample, comprising:

providing an optical assay device, said optical assay device comprising a base comprising absorbent material, and a member comprising an optically active test stack, said member rotatably coupled to said base for rotation between a lowered position where said optically active test stack contacts said absorbent material and a raised position where said optically active test stack does not contact said absorbent material;

applying said test sample to said optically active test stack, wherein said member is In said raised position;

rotating said member to said lowered position;

applying a wash to said optically active test stack;

rotating said member to said raised position;

applying an amplifying reagent solution that amplifies a visual indication of the presence or amount of said analyte to said optically active test stack;

rotating said member to said lowered position;

applying a wash to said optically active test stack; and observing said optically active test stack for the visual indication of the presence or amount of the analyte of interest.

3. The method of claim 1 or 2 further including incubating said optically active test stack after applying said test sample and after applying said amplifying reagent solution.

* * * * *